US00PP20252P3

(12) United States Plant Patent
Sheehan

(10) Patent No.: US PP20,252 P3
(45) Date of Patent: Sep. 1, 2009

(54) GRAPEVINE 'SHEEGENE-12'

(50) Latin Name: *Vitis vinifera*
Varietal Denomination: Sheegene-12

(76) Inventor: Timothy P. Sheehan, 120 Olivewood Ct., Porterveille, CA (US) 93257

( * ) Notice: Subject to any disclaimer, the term of this patent is extended or adjusted under 35 U.S.C. 154(b) by 45 days.

(21) Appl. No.: 11/897,634

(22) Filed: Aug. 30, 2007

(65) Prior Publication Data

US 2009/0064381 P1 Mar. 5, 2009

(51) Int. Cl.
*A01H 5/00* (2006.01)

(52) U.S. Cl. ..... Plt./205

(58) Field of Classification Search ..... Plt./205
See application file for complete search history.

*Primary Examiner*—June Hwu
(74) *Attorney, Agent, or Firm*—Baker Manock & Jensen, PC; Eric C. Cole

(57) ABSTRACT

The new and distinct variety characterized by a dark red-colored, medium sized seedless grape that ripens in early August approximately two weeks later than the Flame Seedless Grape (unpatented) when grown in the San Joaquin Valley of Central California. The grapes of this variety are produced on strong woody stem and branches and are well adapted to commercial handling.

1 Drawing Sheet

Latin name of the genius and species of the plant claimed: The claimed plant relates to a new and distinct variety of *Vitis vinifera* to be known as 'Sheegene-12'.

Variety denomination: This invention relates to a new discovery and asexual reproduction of a new variety of *Vitis vinifera*. The new variety was first hybridized by Timothy P. Sheehan of Porterville, Calif. in late Spring 2000; first flowering occurred in May 2003. The pollen parent is Princess (unpatented) and the seed parent is Red Globe (U.S. Plant Pat. No. 4,787). The new variety was asexually propagated in the dormant season of 2003/2004, bud grafted on Harmony, virus-free rootstock, in a *Vitis vinifera* variety block located near Fowler, Calif. on the west side of Thompson Road, north of Adams Road. The dark red-colored seedless grapes produced by the new variety are medium in size and mature approximately two weeks later then Flame Seedless (unpatented). The new variety has been shown to maintain its distinguishing characteristics through asexual propagation.

The new variety is distinguished from its pollen parent, Princess (unpatented), in that the new variety produces dark red-colored seedless grapes, as compared to the white-colored grapes produced by the pollen parent, Princess (unpatented). The new variety is distinguished from its seed parent, Red Globe (U.S. Plant Pat. No. 4,787), in that the new variety produces seedless grapes, as compared to its seed parent Red Globe (U.S. Plant Pat. No. 4,787), that produces seeded grapes.

BACKGROUND OF THE INVENTION

The present invention relates to a new and distinct variety of grape which will hereinafter be denominated as 'Sheegene-12' and more particularly as a grapevine which produces a dark red-colored seedless table grape that matures in early August in the San Joaquin Valley of Central California. The new invention most closely resembles Flame Seedless (unpatented) but it produces a dark red-colored medium size grape that is sweet, has very good flavor, and matures at least two weeks later.

SUMMARY OF THE INVENTION

The 'Sheegene-12' grapevine is characterized by producing a medium sized, dark red-colored seedless grape with very good flavor that is mature for harvesting and shipment in early August in the San Joaquin Valley of Central California. The new variety can be compared to Flame Seedless (unpatented) but the grapes mature at least two weeks later, among other distinguishing characteristics.

BRIEF DESCRIPTION OF THE DRAWINGS

The accompanying drawing is a colored photograph of the grapes produced by the subject variety; several leaves are displayed as well as a typical section of the vine. Across the top of the color photograph on each side are secondary growth clusters; and in the center is a shoot with leaves and tendrils. Across the middle of the color photograph on the left is a mature grape cluster; and to the right is a mature leaf displaying the bottom surface and petiole. Below the mature grape cluster are four grapes cut in half longitudinally as well as horizontally displaying the flesh and shape. Across the bottom of the color photograph to the left is a mature leaf displaying the topside of leaf and petioles; and to the right is a mature cane displaying tendrils, nodes, and small leaves.

DETAILED BOTANICAL DESCRIPTION

Referring more to the horticultural description of the new and distinct variety of grapevine, the following has been observed under the ecological conditions prevailing at the origin vineyard that is located east of Fowler, Calif. in the San Joaquin Valley of Central California.

All major color descriptions are by reference to the Dictionary of Color by Maerz and Paul, First Edition, published in 1930. Common color names are also used in several instances.

Vine:

*Size.*—5 feet (1.52 meters) in height, 31 to 36 inches (78.74 to 91.44 cm) in width.
*Vigor.*—Very good.
*Chilling requirements.*—Normal for grapevines in the San Joaquin Valley of Central California.
*Figure.*—Wide cordons forming a "T" shaped figure.
*Production capacity.*—Very good.
*Regularity of bearing.*—Regular.

Trunk:

*Size.*—Medium to large; 8½ inches in circumference (21.59 cm); 27 inches (68.58 cm) above graft.
*Surface texture.*—Rough, shaggy.
*Color of bark.*—Pl.7 H7 Cedar +.
*Mature cane color.*—Pl.7 I8 Domingo.
*Nodes.*—Five on canes, 20⅜ inches (51.75 cm) in length.
*Length between nodes.*—3½ to 4½ inches (8.89 to 11.43 cm).
*Lenticel number.*—0.
*Lenticel size.*—0.
*Shoot contour.*—Droopy.
*Tendril number.*—One at node.
*Tendril length.*—2.36 to 5.82 inches (6 to 13½ cm).
*Tendril location.*—At nodes.
*Tendril form.*—Bifurcate.
*Tendril texture.*—Firm, woody.
*Bud shape.*—Triangular.
*Bud size.*—0.35 inches (9 mm) in width; 0.35 inches (9 mm) in length.
*Bud break date.*—N/A.

Branches:

*Size.*—Medium to large; 7 inches (17.78 cm) in circumference.
*Surface texture.*—Slightly rough.
*Color* (*One year older wood*).—Pl. 17 I7 Laurel Oak.
*Surface texture* (*mature canes*).—Smooth.

Leaves:

*Size.*—Medium to large.
*Density.*—Dense.
*Average length.*—4.92 to 5.59 inches (12.5 to 14.2 cm).
*Average width.*—6.89 to 7.28 inches (17.5–18.5 cm).
*Texture.*—Upper surface is smooth; lower surface is glabrous.
*Color* (*upward disposed surface*).—Pl.23 J8— Mt. Vernon Green.
*Color* (*downward disposed surface*).—Pl.20 K7 Near Piquant Green. Color (leaf vein). Pl.17 L7 Viridine Y.
*Marginal form.*—Generally slightly undulate.
*Leaf vein* (*thickness*).—0.079 inches (2 mm).
*Leaf margin.*—Toothed.
*Glandular characteristics.*—0.
*Petiole size.*—Large.
*Petiole length.*—4.84 to 5.31 inches (12.3 to 13.5 cm).
*Petiole thickness.*—0.12 to 0.197 inches (3 to 5 mm).
*Petiole color.*—Downwardly disposed surface, Pl.20 L5 Lettuce Green; upwardly disposed surface, Pl.7 L6 India Red, Arabian Red and Red Robin.
*Petiole sinus form.*—Reverse "U" shape.
*Stem gland form.*—0.
*Stem gland position.*—0.
*Stem gland pattern.*—0.
*Lobe average.*—Four.
*Tooth size.*—0.47 to 0.51 inches (12 to 13 mm) in width; 0.28 to 0.31 inches (7 to 8 mm) in length) inches (7 to 8 mm) in length.
*Tooth number.*—Four large between lobes.
*Tooth shape.*—Triangular.

Inflorescence:

*Size.*—Cluster is 6 to 7 inches (15.24 to 17.78 cm) in length.
*Number borne per spur.*—Two.
*Number borne per vine.*—20 to 24.

Flowers:

*Flower buds* (*size*).—Small.
*Flower buds* (*surface*).—Glabrous.
*Flower buds* (*quantity*).—Moderate.
*Date of bloom.*—Apr. 27, 2007.
*Date of full bloom.*—May 7, 2007.
*Size of bloom.*—0.12 inches (3 mm).
*Petal color.*—Pl. 20 L9— Eden green.
*Petal size.*—0.08 inches (2 mm).
*Pistil color.*—Pl. 17 L7— Viridine y.
*Amount of pollen.*—Not available.
*Date of first visible berries.*—May 7, 2007.

Fruit:

*Seeds.*—None.
*Cap stem pedicel.*—0.24 to 0.31 inches (6 to 8 mm).
*Berry weight.*—8.52 grams.
*Juice color.*—Pl.13 L5 Bistro Green.
*Cluster size.*—Medium to large.
*Cluster average weight.*—511.2 to 710 grams (1 lb. 2 oz. to 1 lb. 9 oz.).
*Cluster average length without stem.*—8.66 to 10.04 inches (22 to 25 cm).
*Cluster average width.*—5.31 to 5.91 inches (13.5 to 15 cm).
*Cluster form.*—Conical.
*Stem.*—Generally variable; 1.81 to 1.97 inches (4.6 to 5 cm).
*Stem caliper.*—0.197 inches (5 mm).
*Berry size.*—Medium to large.
*Berry size* (*average dimension along longitudinal axis*) .—0.79 to 0.98 inches (20 to 25 mm).
*Berry size* (*average dimension along transverse axis*) .—0.75 to 0.87 inches (19 to 22 mm).
*Berry shape.*—Ovate.
*Berry number.*—60 to 84 berries per bunch.

Flesh:

*Flesh color.*—Pl.13 L7 Tinsel Deepstone.
*Juice production.*—Very good.
*Flavor.*—Very good.
*Armoa.*—Mild.
*Texture.*—Firm.
*Ripening.*—Even.
*Eating quality.*—Very good.

Skin:

*Skin thickness.*—Medium.
*Texture.*—Tough.
*Blush color.*—From Pl.55 L8 Rubient to Pl.56 E8 Burgundy.
*Ground color.*—Pl.13 L7 Tinsel Deepstone.
*Lenticel.*—0.
*Use.*—Fresh Market.
*Keeping quality.*—Unknown.
*Resistance to disease.*—None observed.
*Harvesting and shipment.*—Early August in the San Joaquin Valley of Central California.

*Shipping and handling quality.*—Moderate.U.S.D.A. Hardiness Zone: Zones 8 and 9.

Having thus described and illustrated our new variety of grapevine, we claim:

1. A new variety of grapevine to be known as 'Sheegene-12', substantially as illustrated and described, characterized principally by its production of dark red-colored, medium sized seedless grapes, that mature approximately two weeks later in the season of ripening than does the Flame Seedless Grape (unpatented) which it closely resembles.

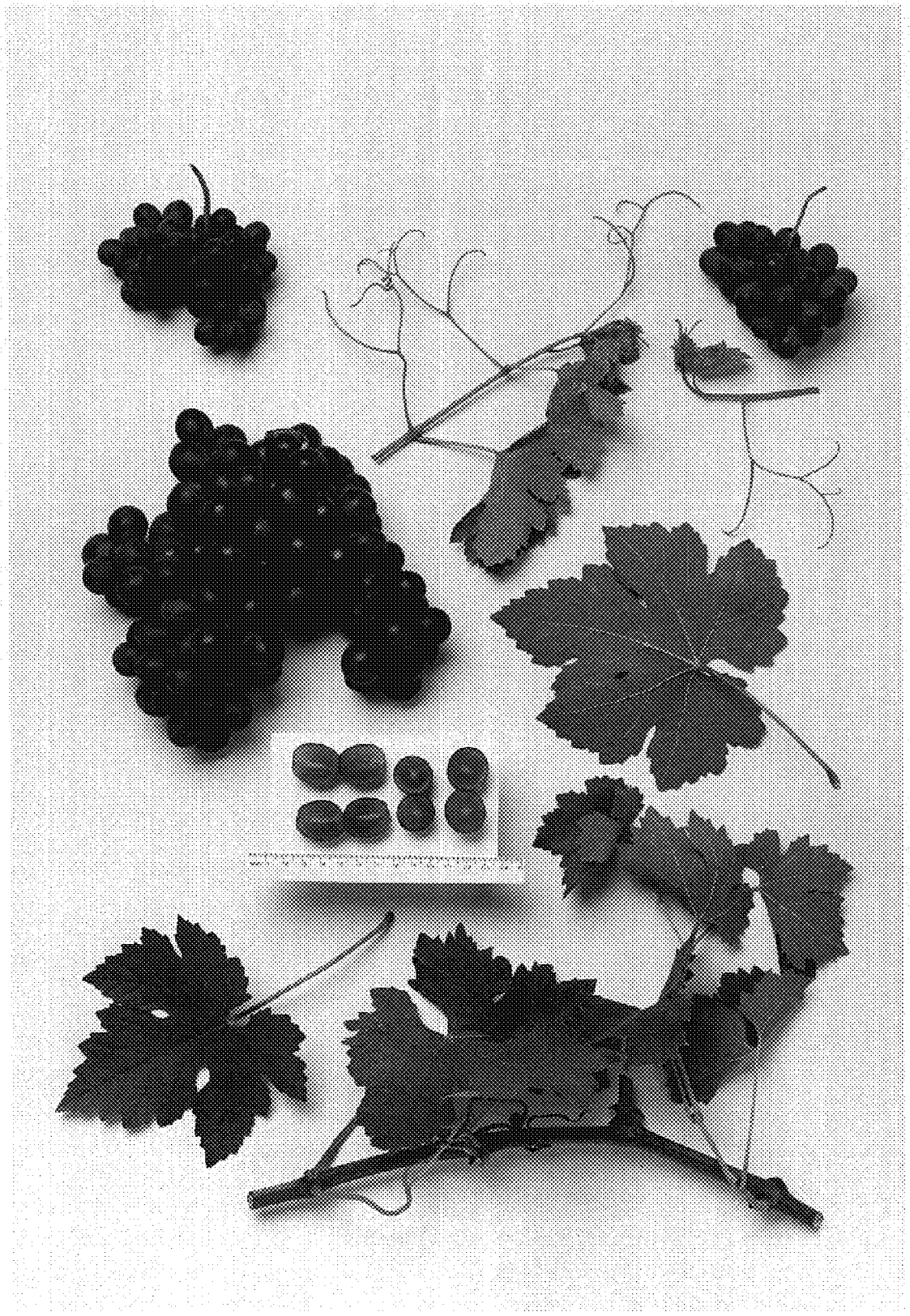

* * * * *